United States Patent [19]

Duffy et al.

[11] Patent Number: 5,605,933
[45] Date of Patent: Feb. 25, 1997

[54] RETINOID CONJUGATE COMPOUNDS AND METHODS FOR TREATING OF SKIN AGING

[75] Inventors: John A. Duffy, West Milford, N.J.; Janice J. Teal, Suffern; Mark S. Garrison, White Plains, both of N.Y.; George P. Serban, Ridgefield, Conn.

[73] Assignee: Avon Products, Inc., Suffern, N.Y.

[21] Appl. No.: 504,693

[22] Filed: Jul. 20, 1995

Related U.S. Application Data

[63] Continuation of Ser. No. 167,424, Dec. 15, 1993, abandoned.

[51] Int. Cl.$^6$ .......................... A61K 31/07; A61K 31/19; A61K 31/22
[52] U.S. Cl. ...................... 514/557; 514/725; 514/847
[58] Field of Search ..................................... 514/847, 557, 514/725; 568/626

[56] References Cited

U.S. PATENT DOCUMENTS 5,153,230  10/1992  Jaffery ........................................ 514/847
5,182,396  1/1993  Tachibana .

FOREIGN PATENT DOCUMENTS

| 0434628 | 6/1991 | European Pat. Off. . |
| 0508848 | 10/1992 | European Pat. Off. . |
| 6366160 | 3/1988 | Japan . |
| 4210686 | 7/1992 | Japan . |
| 0670951 | 7/1989 | Switzerland . |

*Primary Examiner*—Shean C. Wu
*Attorney, Agent, or Firm*—Hopgood, Calimafde, Kalil & Judlowe

[57] ABSTRACT

Skin aging and related conditions can be effectively treated with a conjugate of a retinoid and a bioactive organic acid preferably selected from among alpha-hydroxy acids, beta-hydroxy acids, and keto-acids; preferred conjugates include retinyl glycolyl ether and retinyl glycolate (as either the ester or reverse ester).

7 Claims, No Drawings

RETINOID CONJUGATE COMPOUNDS AND METHODS FOR TREATING OF SKIN AGING

This is a continuation of application Ser. No. 08/167,424, filed Dec. 15, 1993, now abandoned.

BACKGROUND OF THE INVENTION

1. The Field of the Invention

The present invention relates to conjugates of retinoids with organic acids and to the use of such compounds in the treatment of skin aging.

The UVL component of sunlight is responsible for triggering molecular changes that damage biological tissues including the skin. It is postulated that one mechanism for sun-induced aging results from the generation of free radicals in the skin. One proposed pathway to free radical generation, the so-called Haber-Weiss reaction (shown in Scheme I), is a chemical pathway which generates the most reactive free radical species, the hydroxyl radical.

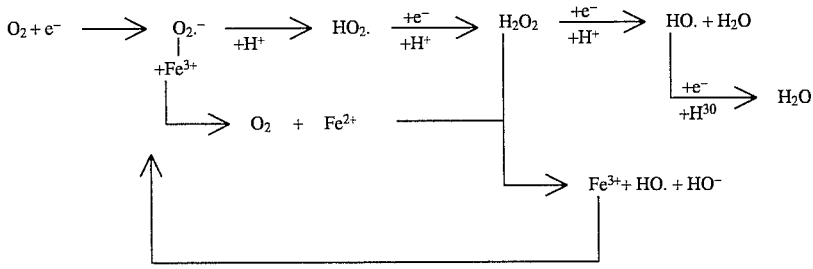

2. The State of the Art

Skin aging is accompanied by a number of morphophysiological changes which are described in the literature. See, e.g., B. A. Gilchrest, *J. Cutaneous Aging Cosmet. Dermatol.*, 1:1–3 (1988), and *Arch. Dermatol.*, 115:1343–1346 (1979). At the physiological level, skin aging is accompanied by a decrease in at least one critical skin function, such as epidermal turnover, healing, clearance of chemicals from the dermis, water regulation, sensory perception, mechanical protection, immunocompetence, vascular reactivity, blood flow, sweat gland function, turgor, sebum production or Vitamin D synthesis.

At the morphological level, a decline in critical physiological functioning is associated with a loss in the normal pattern of corneocyte desquamation, epidermal thinning and/or the presence of atypical epidermal cells. Other characteristics include a reduction in the height of rete ridges along with a corresponding effacement of dermal papillae, a general weakening of the dermo-epidermal junction, excessive accumulation of elastin and a loss of collagen and other ground substances, a decrease in dermal volume (turgor), pigmentary disorders, attrition of capillary vessels, chronic inflammation and the occurrence of benign and/or malignant tumors. Some of the clinical manifestations of these morphological changes which are relevant to cosmetic appearance and dermal health include a rough, flaky and/or dry skin surface, itching, excessive wrinkling, sagging, loss of elasticity, sallow color, mottled pigmentation, thinning hair, nail brittleness and, in some cases, skin growths.

The etiological bases underlying skin aging are only partially understood. But, it is recognized that the effect of ultraviolet light (UVL), especially from the sun, constitutes a significant factor in the acceleration of skin aging. Several studies have shown that skin which has been exposed to sunlight undergoes aging sooner than unexposed areas in the same individual. By comparing the histological and functional characteristics of exposed and unexposed skin, investigators have observed differences between chronological and accelerated premature aging. See, e.g., W. Montagna, *J. Inves. Dermatol.*, 73:47–53 (1979); B. A. Gilchrest, *J. Invest. Dermatol.*, 80:81s–85s (1983); and B. A. Gilchrest, *J. Invest. Dermatol.*, 73:59–66 (1979).

wherein $\frac{1}{2}O_2$ is singlet oxygen or the superoxide ion, $HO_2$ is the hydroperoxyl radical, $H_2O_2$ is hydrogen peroxide, $HO$ the hydroxy radical and $H_2O$ is water. In this reaction, electrons ($e^-$) are gained through the oxidation of metals such as iron, copper and zinc, which are typically present in the skin. The hydrogen atoms are gained through the destructive oxidation of biological molecules essential to the normal function of cells, tissues and organs, such as lipids, proteins, DNA, RNA, and enzymatic cofactors. There are numerous studies showing how the oxidation of these essential molecules is detrimental to the skin, in both the long term and short term.

The retinoids are biologically active compounds involved in essential functions such as vision, embryonic development and the growth and maintenance of normal skin. The art teaches that topical application of skin preparations containing retinoids provides a significant improvement in clinical appearance. See, for example, U.S. Pat. Nos. 4,603,146 and 4,877,805. Additionally, topical application of retinoids provide improvement with respect to several histological parameters, such as thickening of the epidermis including the stratum granulosum, an increase in the height of rete ridges and the number of dermal papillae, a gradual displacement of age-related deposition of dermal elastin by collagen and peptidoaminoglycans, normalization of melanocyte function and an increase in the number of dermal fibroblasts. See, e.g., A. S. Zelickson, *J. Cutaneous Aging Cosmet. Dermatol.*, 1:41–47 (1988); J. S. Weiss, *JAMA*, 259:527–532 (1988); J. Bhawan, *Arch. Dermatol.*, 127:666–672 (1991); and L. H. Kligman, *Connect. Tissue Res.*, 12:139–150 (1984). U.S. Pat. No. 4,603,146 also describes the use of Vitamin A acid for retarding skin aging, and U.S. Pat. No. 4,877,805 describes the use of retinoids generally for the same purpose (the disclosures of which are both incorporated herein by reference).

The skin is a target for and requires retinoids. This conclusion stems from the fact that Vitamin A deficiencies lead to skin lesions. Additionally, skin cells, such as fibroblasts and keratinocytes, contain high-affinity cytosolic receptors for retinoids, thus further demonstrating the target nature of these skin cells.

It is well-known that therapeutic doses of topically applied retinoids frequently cause skin irritations which interfere with treatment. To solve this problem, the art has resorted to conjugating retinoids with glucuronic acid. See, for example, U.S. Pat. No. 4,855,463, which discloses water-soluble glucuronic acid derivatives of Vitamin A (formula I) for improved metabolic uptake and S. Chen, *J. Invest. Dermatol.*, Abstract, 98:560 (1992) which describes conjugates of retinoids and acetaminophen (formula (II)). In both cases, conjugation was achieved by attaching the other molecule to carbon-15 of the retinol structure.

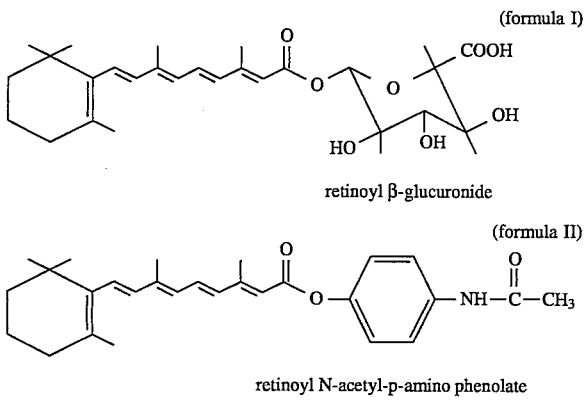

retinoyl β-glucuronide (formula I)

retinoyl N-acetyl-p-amino phenolate (formula II)

U.S. Pat. No. 4,216,224 describes retinyl esters of hydroxy acids, hydroxy amides or hydroxy acid esters for use in treating psoriasis. And, U.S. Pat. No. 5,124,356 describes ester and amide conjugates of trans-retinoids, although the molecule conjugated with the retinoid is not described as providing any separate therapeutic benefit. EP-A2-0 391 033 further describes the preparation of retinal derivatives, especially acetals and hemiacetals, useful in treating a variety of skin conditions.

JP-A 63-66160/1988 describes the preparation of a retinoyl ester of 1-ascorbic acid which is taught to be useful for increasing the activity of blood vessel endotheliocyte plasminogen activators, and for increasing the hydrophilic properties of retinol and retinoic acid to reduce instability of the composition due to oxidation. In vitro data on endotheliocyte cultures showed increased activity of plasminogen activator, but no methods or compositions for administration are disclosed.

JP-A 4-210686/1992 describes a method for the manufacture of tocopheryl retinoate. This compound is taught to be useful for treating skin ulcers (e.g., JP-A 61-207332) and for preventing the roughening of skin (e.g., JP-A 51-73137). U.S. Pat. No. 5,182,396 discloses that 1-hydroxy Vitamin D esters with Vitamin A acid are useful for treating cutaneous ulcers and tumors.

Carboxylic acids are also useful in the treatment of aging skin, especially alpha- and beta-hydroxy acids and keto-acids. These are generally referred to as AHAs (Alpha-Hydroxy Acids). See, e.g., U.S. Pat. Nos. 3,920,835, 4,045, 559, 4,053,630 and 4,363,815, the disclosures of which are all incorporated herein by reference. Additionally, U.S. Pat. No. 4,194,007 describes α-hydroxyretinoic acid and α-ketoretinoic acid as derivatives of retinoic acid.

These AHAs improve the clinical appearance and mechanical properties of aging skin. A normalization in the pattern of epidermal keratinization and a reduction in the cohesive forces acting between keratinocytes and corneocytes have also been reported after treatment with AHAs (E. J. Van Scott, *J. Acad. Dermatol.*, 11:867–879 (1984)). Other investigators have observed such benefits as wrinkle reduction after topical application of AHAs. They postulate that AHAs stimulate collagen and glycosaminoglycan synthesis by cultured fibroblasts (F. D. Dial, *Cosmetic Dermatology*, 5:32–34 (1990)). AHAs also increase the production of collagen and peptidoaminoglycans (R. M. Lavker, *J. Am. Acad. Dermatol.*, 26:535–544 (1992)), thereby further improving the general topographical appearance and viscoelastic behavior of skin.

The action by which AHAs improve the clinical appearance and mechanical properties of skin is not well-understood. One feature of aging skin is hyperkeratinization, a condition in which the corneocytes adhere in excess, thereby creating a thickened stratum corneum and a dry appearance. The forces responsible for the adhesion of corneocytes are non-covalent in nature and evidence exists that both ionic and hydrophobic interactions are involved. In the case of ionic interactions, calcium ions are believed to bridge adjacent corneocytes by forming complexation bonds between cholesteryl sulfate residues that are firmly anchored to the corneocyte cell wall (L. J. Shapiro, *Lancet*, 1:70–72 (1978)). Since ionic interactions are pH dependent, AHAs may decrease corneocyte cohesion by temporarily opening up calcium bridges. However, an explanation of activity based on pH alone is not satisfactory. Earlier work aimed at studying the relationship between the chemical structure of these agents and their ability to influence the viscoelastic behavior of the stratum corneum clearly indicates that, among the series of AHAs studied, those having hydroxy groups in the alpha position consistently lowered this parameter (M. Takahashi and Y. Machida, *J. Soc. Cosmet. Chem.*, 36:177–187 (1985)). The lower the viscoelastic modulus, the less force is required to cause deformation (i.e., the softer the stratum corneum).

AHAs are known to produce a long-lasting decrease in the elastic modulus of skin. This means softening and, with regular use, a normalization in the pattern of corneocyte desquamation. Recent work shows that these beneficial effects are optimized after the AHAs are conjugated with linear aliphatic chains having eight to ten carbons (e.g., D. B. Hagan et al., "A study of the structure-activity relationships present in skin active agents," *Int'l J. Cosmetic Sci.*, 15, 163–173 (1993), the disclosure of which is incorporated herein by reference).

It will be appreciated that a range of compounds have been considered for the treatment of skin aging. While there are theoretical, if not observed, benefits derived from these compounds, problems relating to stability, toxicity and dermal penetration still exist. These problems limit the availability of useful therapies for skin aging.

SUMMARY OF THE INVENTION

It is among the objects of this invention to provide a new class of compounds useful in the treatment of aging skin and to provide methods for the use of such compounds in the treatment of aged and aging skin. Particular benefits achieved by the present invention include increased stability of the active compound, improved dermal penetration and a higher therapeutic index (i.e., selectivity, typically defined as TD50/ED50 or LD50/ED50).

The present invention specifically provides a class of multi-functional conjugated retinoids, dimers of a retinoid and another bioactive ingredient selected from the group consisting of organic acids, preferably a bioactive organic acid, and especially those known generally as AHAs. When used for treating aged skin, these novel conjugates provide a higher therapeutic index than any of the classes of agents discussed in the Background section of this disclosure, whether applied individually or in combination.

The present invention also provides a pharmaceutical composition which comprises an amount of the novel conjugate effective to provide a benefit to a morphological and/or clinical aspect of aging skin and a compatible carrier therefor; these aspects are described above in the Background section. In a preferred embodiment, the carrier is cosmetically acceptable, if not dermatologically acceptable.

The invention also provides a method for treating aging skin of a patient having such aged skin, which comprises providing the novel conjugate of this invention as a composition comprising a mixture of the conjugate and a cosmetically acceptable carrier therefor, and applying said composition to the patient such that the amount of conjugate applied is effect to benefit a morphological and/or clinical aspect of the patient's aging skin.

DETAILED DESCRIPTION OF SPECIFIC EMBODIMENTS

The present invention is directed to novel conjugates of retinoids. As used herein, the term "retinoid" includes Vitamin A (retinol) and derivatives such as retinoic acid (e.g., tretinoin, also sold as Retin-A brand by Johnson & Johnson Co., New Brunswick, N.J.), retinal (Vitamin A aldehyde), 3,4-didehydroretinol (Vitamin $A_2$), and cosmetically acceptable derivatives thereof, such as Vitamin A acetate and Vitamin A palmirate, and other esters or reverse esters (or salts thereof), ethers, aldehydes, alcohols, and the like. Retinol has the structure of formula II which is shown below.

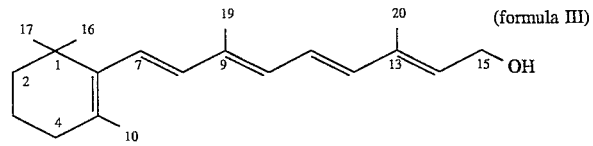

The retinoid is conjugated with a bioactive agent selected from organic acids, especially those which are cosmetically acceptable, and particularly those which have a beneficial effect on the appearance and/or properties of aging skin. It is preferred that the retinoid be conjugated with a low molecular weight organic acid (i.e., one having not more than about 10 carbon atoms). Is preferred that the linkage between the retinoid and the organic acid be through an ester, reverse ester, ether or amide bond, and most preferably the linkage is an ether bond. It is believed that these types of bonds can be cleaved by non-specific, ubiquitous hydrolytic enzymes present in large amounts in the viable dermal tissues, and to a lesser extent in the stratum corneum. While not desirous of being constrained to a particular theory, after delivery to the dermal tissues, these novel conjugates are believed to hydrolyze in vivo and yield an active retinoid and active AHA agent. Both compounds provide anti-aging effects when made available to the skin.

The novel conjugates of this invention can be made using organic acids or their derivatives, such as aldehydes, ketones, alcohols, esters, reverse esters, anhydrides, acyl halides, and salts thereof, and preferably those which are bioactive (although, in some situations, it may be desirable to provide an organic acid which is relatively inert). The organic acid preferably has from 2 to 24 carbon atoms, more preferably from 4 to 18 carbon atoms, most preferably from 3 to 12 carbon atoms, and especially including 6 to 10 carbon atoms. Particular α-hydroxy organic acids suitable for use with this invention include, as examples, glycolic, lactic, citric, tartaric, mandelic, benzilic, and malic acids. Particular oxoacids suitable for use with this invention include, for example, glyoxylic and pyruvic acids. Other carboxylic acids, such as succinic, fumaric, oxalic, and salicylic acids, are also suitable for use with this invention. Other suitable organic acids include those which are normal cellular constituents. More preferably, the organic acid is selected from among alpha-hydroxy acids, beta-hydroxy acids, and keto-acids (generally known as AHAs). AHAs generally contain from two to five carbon atoms in their aliphatic residue and are highly ionized; that is, they are strongly acidic.

Derivatives of organic acids which are suitable in this invention include substitutions on the acid, and especially substitutions at the 2-position (e.g., the α-position of an AHA). Exemplary derivatives include 2-thio derivatives (e.g., wherein the hydroxyl group of the AHA is substituted with a thiol group), thioalkyl and thioalkenyl derivatives (e.g., those substituted at the 2-position of a carboxylic acid, and especially of a hydroxycarboxylic acid), keto derivatives, methoxy derivatives, and halogen derivatives (including F, Cl, Br, and I).

The organic acid may generally be saturated, unsaturated, or polyunsaturated, with double bonds independently in cis- or trans- configurations. Further, the organic acid can be straight- or branched-chain, substituted or unsubstituted, acyclic, cyclic, or heterocyclic, and including aromatic compounds. Also generally suitable are organic acids which are liquid at ambient pressure and temperature (i.e., about 25° C. and 1 atm.).

After topical application of an AHA, skin surface pH is temporarily lowered from a normal level of about 5 to a more acidic level of about 3. The localized acidity can result in stinging, particularly on the face where microfissures are more common than on other parts of the body. Because charged molecules penetrate the cutaneous barrier very slowly, it may require several hours for the increased surface acidity to be neutralized, which would end the stinging and discomfort to the patient.

Conjugation of a short chain carboxylic acid with a retinoid, especially where the acid is conjugated via the carboxylate moiety, largely quenches the ability of the acidic residue to become deprotonated. Accordingly, the novel conjugates of this invention provide improved treatment by alleviating acidification of the skin and the accompanying stinging and other discomfort, even when applied to the facial area.

Charged molecules, such as AHAs, are known to be poor skin penetrators because, ordinarily, they cannot partition and diffuse through the lipid-rich lamellae present in the intercorneocyte spaces. Water-soluble AHAs have low rates of percutaneous absorption for this reason. By conjugating these acids with the larger, more lipophilic retinoid, they tend to pass through the intact domains of the stratum corneum rather than partition from the formulation and into the microfissures.

The synthesis of the novel conjugates of this invention may require conjugating the lipophilic retinoid with a lipophobic molecule such as any of the AHAs. Conjugates having ester or even ether linkages may be hydrolyzed in water, thereby making synthesis more difficult. Accordingly, it can be beneficial if not desirable to protect active moieties on the AHA conjugated with the retinoid. This precaution facilitates formation of the conjugate bond and/or facilitates solubilizing both of the reactants (retinoid and AHA) in a common medium. For example, whereas glycolic acid (hydroxy ethanoic acid) and acetic acid (ethanoic acid) are both soluble in water, the bromoacetic acid methyl ester used in the synthesis exemplified above is insoluble in water, but soluble in alcohol and ether suitable as the reaction medium.

In various synthesis of conjugates within the scope of this invention, it may be necessary to protect one or more reactive groups, such as hydroxyl groups. Such methods of protection for particular substituents are known to those skilled in the arts of organic synthesis.

In practicing the present invention, it should be appreciated that conjugate formation may require a precursor or derivative of the organic acid required for the synthesis. The skilled artisan can readily choose a synthesis scheme and a suitable precursor or derivative for the production of the desired conjugate.

In preparing a composition for use in treating skin aging, one or more conjugates (which are chemically compatible) are provided in a cosmetically or pharmaceutically acceptable vehicle. The amount of the conjugate will preferably range between about 0.001% and 4% by weight (unless otherwise noted, all fractional amounts are expressed in weight percent), more preferably between about 0.01% and 1.0%, and most preferably between about 0.05% and 0.25% of the composition. The composition should be applied between one and three times each day to an affected area.

A cosmetically acceptable organic acid can optionally be present independently in the composition in an amount, preferably a bioactively effective amount, of 0.1% to 5.0%; the addition of an AHA is a preferred embodiment. When one or more such organic acids are present in the composition, the pH of the composition may need to be raised to more neutral levels by the addition of an alkaline material (e.g., sodium, potassium, or ammonium hydroxide).

Suitable vehicles or carriers for storage and/or delivery of the novel conjugates of this invention may be provided in liquid, ointment, salve, spray, poultice or other forms, and will preferably have a lipophilic character. Suitable carriers include petrolatum, triglycerides, various esters, fatty alcohols, alkylene glycols, and ethanol, of which polypropylene glycol, and polyethylene glycol are most preferred; if desired, compatible combinations of these vehicles are also suitable.

Carrier systems for topical delivery include lotions, ointments, salves, creams, gels, foams, sprays (both mists and aerosols), patches, masks and the like. The vehicles are present as needed for the desired delivery system. Additional components may be added according to conventional practice. For example, the final composition may contain various colorants, fragrances, thickeners (such as xanthan gum), preservatives, humectants, surfactants, dispersants and the like, including typical botanical extracts such as those derived from Witch Hazel, chamomile, and the like (e.g., those having an astringent, antiseptic, or other desired effect). The composition may likewise include a penetration enhancer such as DMSO (dimethyl sulfoxide). It may also include one or more additional active ingredients (such as an antibiotic, anesthetic or growth factor).

The invention will be further illustrated by means of the following example, which is not meant to limit this invention to the particular materials, conditions and products described.

EXAMPLE 1

Preparation of Retinoid/Glycolic Acid Ether Conjugate

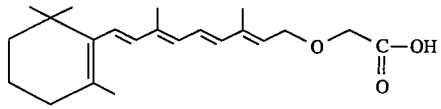

In a dark room under dim red light, retinol acetate (120 g., 366 mmol, obtained from BASF Corp., Parsippany, N.J.). was dissolved in 1.5 L of methanol under an argon atmosphere. Solid potassium carbonate (151.5 g., 1098 mmol) was added with stirring. After seven hours of stirring, the reaction mixture was filtered through a coarse fritted filter to remove solids. Methanol was then removed by evaporation. Diethyl ether was added and the mixture was washed first with distilled water (although tap water could be used), and then washed with brine (i.e., a saturated sodium chloride solution). The washed ether layer was dried over $MgSO_4$ and $Na_2SO_4$, filtered and then distilled under reduced pressure to produce retinol (101 g., 96% yield). Residual oil was crystallized from hexane using a seed crystal of authentic retinol. This general synthesis of retinol from retinol acetate has been described by J. J. Platther, *J. Am. Chem. Soc.*, 94, 8613 (1972).

Under dim red light, sodium hydride (60% dispersion in mineral oil, 18.4 g., 459 mmol) was placed in an r.b. flask under argon. Hexane (freshly distilled from $CaH_2$) was used to wash the sodium hydride three times to remove residual mineral oil. Tetrahydrofuran (THF, 350 ml) was added to the sodium hydride with stirring to obtain a suspension. The retinol (101 g.) produced in the preceding step, plus 19 g. of previously obtained retinol crystals (total 120 g., 418 mmol) were dissolved in 300 ml THF. The THF solution of retinol was slowly added to the sodium hydride suspension while the suspension was stirred and maintained in an ice bath. Evolution of hydrogen gas was noted. After this addition, the ice bath was removed and stirring was continued for approximately 30 minutes. A dropping funnel was charged with methyl bromoacetate (97%, 41.76 ml, 430 mmol) and 100 ml THF. The methyl bromoacetate solution was added drop-wise at such a rate that the reaction temperature was maintained at not greater than approximately 30° C. This procedure required approximately two hours and the mixture was stirred for an additional two hours. The product was retinyl acetate ether which resulted from alkylation of the previously formed retinol. The alkylation of retinol with methyl bromide has been described by B. A. Stoochnoff, *Tetrahedron Lett.*, Vol. 21 (1973) and C. A. Brown, *Synthesis*, Vol. 434 (1974).

Under dim red light, any residual sodium hydride remaining after the alkylation step was quenched by the addition of a few milliliters of methanol. Water (400 ml) was carefully added to the reaction mixture. Lithium hydroxide (30 g., 1254 mmol) was then added. After 15 minutes, the reaction was homogeneous. After stirring for two additional hours, the reaction flask was placed on a rotary evaporator to partially remove the THF. The basic aqueous phase was extracted three times with ether to remove the non-base soluble materials, such as unreacted retinol. The aqueous layer was then acidified to a pH of 3 with 4N HCL at 0° C. and extracted four times with ether to give the crude saponified product (79 g., 220 mmol; 53% yield). Analysis by NMR, UV-VIS and mass spectroscopy confirmed that the product was retinol glycolic ether (retinyl glycolyl ether).

EXAMPLES 2–6

The retinyl glycolic ether produced in claim 1 is made into a variety of cosmetically acceptable formulations, including a cream, a gel, a lotion, a toner, and an ointment as shown below. All amounts given are weight fractions unless otherwise noted.

| Cream | |
|---|---|
| Cetyl alcohol | 2.00 |
| Glyceryl monostearate | 2.50 |
| White Petrolatum | 5.00 |
| Octyl Palmitate | 8.00 |
| Steareth-2 | 1.00 |
| PEG 40 Stearate | 1.50 |
| CARBOMER 940 | 0.75 |
| Triethanolamine (99%) | 0.75 |
| Retinyl Glycolyl Ether | 0.50 |
| Water | q.s. to 100% |
| Gel | |
| Propylene Glycol | 5.00 |
| Glycerin | 3.00 |
| Alcohol | 10.00 |
| CARBONER 940 | 0.50 |
| Triethanolamine | 0.50 |
| Retinyl Glycolyl Ether | 2.00 |
| Water | q.s. to 100% |
| Lotion | |
| Xanthan Gum | 0.25 |
| Hydroxyethyl cellulose | 0.40 |
| Propylene Glycol | 5.00 |
| Caprylic/Capric Triglyceride | 8.00 |
| Steareth-2 | 1.50 |
| PEG 40 Stearate | 2.00 |
| Retinyl Glycolyl Ether | 0.20 |
| Glycolic Acid | 2.00 |
| Ammonium Hydroxide | q.s. to $3 \leq pH \leq 4$ |
| Water | q.s. to 100% |
| Toner | |
| SD alcohol | 35.00 |
| Glycerin | 3.00 |
| Disodium EDTA | 0.20 |
| Botanic Extracts | 1.00 |
| Retinyl Glycolyl Ether | 0.01 |
| Lactic Acid | 1.00 |
| Ammonium Hydroxide | q.s. to $3 \leq pH \leq 4$ |
| Water | q.s. to 100% |
| Ointment | |
| White Petrolatum | 97.6 |
| Retinyl Glycolyl Ether | 2.4 |

Various modifications and alterations to the present invention may be appreciated based on a review of this disclosure. These changes and additions are intended to be within the scope and spirit of this invention as defined by the following claims.

What is claimed is:

1. A method for the treatment of aged and aging skin, which comprises topical application of an effective amount of a conjugate of a retinoid with a bioactive compound selected from the group consisting of organic acids having from 2 to 24 carbon atoms.

2. The method as defined by claim 1, wherein the organic acid is selected from the group consisting of α-hydroxy acids, β-hydroxy acids, and keto-acids.

3. The method as defined by claim 1, wherein the organic acid is an α-hydroxy acid.

4. The method as defined by claim 3, wherein the α-hydroxy acid is an acid selected from the group consisting of glycolic, lactic, citric, succinic, fumaric, oxalic and malic acids.

5. The method as defined by claim 1, wherein the conjugate is an ester, reverse ester, or ether between a retinoid and a compound selected from the group consisting of glycolic acid, lactic acid, citric acid, succinic acid, fumaric acid, oxalic acid, and malic acid.

6. The method as defined by claim 1, wherein said conjugate is applied in the form of a composition comprising 0.05% to 5% of said conjugate and an acceptable topical carrier therefor.

7. The method as defined by claim 6, wherein said composition comprises 0.3% to 0.6% of said conjugate.

* * * * *